United States Patent
Beer-Romero et al.

[11] Patent Number: 5,858,987
[45] Date of Patent: Jan. 12, 1999

[54] E6AP ANTISENSE CONSTRUCTS AND METHODS OF USE

[75] Inventors: Peggy L. Beer-Romero, Arlington; Giulio Draetta, Winchester; Mark Rolfe, Newton Upper Falls, all of Mass.

[73] Assignee: Mitotix, Inc., Cambridge, Mass.

[21] Appl. No.: 435,637

[22] Filed: May 5, 1995

[51] Int. Cl.$^6$ .......................... A61K 48/00; C07H 21/04; C07H 21/02; C12Q 1/68
[52] U.S. Cl. .......................... 574/44; 536/24.5; 536/24.3; 536/24.33; 536/23.1; 435/6; 435/5; 435/91.2
[58] Field of Search .................................. 435/6, 5, 91.2; 536/24.3–33, 23.1, 24.5; 514/44

[56] References Cited

U.S. PATENT DOCUMENTS 5,457,189 10/1995 Crooke et al. .......................... 536/24.5
5,532,348 7/1996 Huibregtse et al. ..................... 536/23.5

OTHER PUBLICATIONS

Gutierrez et al. The Lancet 339:715–721, 1992.
Gura, Science 270:575–577, 1995.
Freeman et al. Advanced Drug Delivery Reviews 12: 169–183, 1993.
James, Antiviral Chemistry and Chemotherapy, vol. 2: 191–214, 1991.
Rolfe et al. PNAS 92:3264–3268, 1995.
Scheffner et al, Cell 75:495–505, 1993.

*Primary Examiner*—Stephanie W. Zitomer
*Assistant Examiner*—Dianne Rees
*Attorney, Agent, or Firm*—Matthew P. Vincent; Beth E. Arnold; Foley, Hoag & Eliot LLP

[57] ABSTRACT

The present invention relates to the discovery that antisense nucleic acids complimentary to an E6AP gene can be used to regulate cellular p53 levels. In general the invention features E6AP antisense constructs which, by inhibiting E6AP activity, can modulate cellular p53 levels in both p53+ transformed cells and in normal cells. The invention also provides methods for treating papillomavirus (PV) induced condition, methods for regulating cellular p53 levels and methods for regulating cellular proliferation.

83 Claims, 1 Drawing Sheet

*FIG. 1*

E6AP ANTISENSE CONSTRUCTS AND METHODS OF USE

BACKGROUND OF THE INVENTION

A proteolytic pathway that has been implicated to play a major role in selective degradation of abnormal and short-lived proteins requires the covalent attachment of ubiquitin to a target protein prior to degradation (for recent reviews see Finley and Chau (1991) *Annu. Rev. Cell Biol.* 7, 25–69; Jentsch et al.(1991) *Biochim. Biophys. Acta* 1089, 127–139; and Hershko and Ciechanover (1992) *Annu. Rev. Biochem.* 61, 761–807). Ubiquitin is a highly conserved protein of 76 amino acids found only in eukaryotes. The basic enzymatic reactions involved in the ubiquitination of proteins are well characterized. Ubiquitin is first activated by the E1 enzyme in an ATP-dependent step in which a thioester is formed between the active site cysteine residue of E1 and the C-terminal glycine of ubiquitin. The activated ubiquitin is transferred to a cystein residue of ubiquitin-conjugating (E2) enzymes, which then catalyze the formation of an isopeptide bond between the C-terminal glycine of ubiquitin and the $\epsilon$-amino group of a lysine residue on a target protein. Ubiquitin also becomes conjugated to itself via a lysine residue at position 48 of ubiquitin, resulting in the formation of multiubiquitin chains (Chau et al. (1989) *Science* 243, 1576–1583). Finally, multiubiquitinated proteins serve as targets that are recognized and degraded by an ATP-dependent protease complex.

Some members of the E2 family are able to ubiquitinate certain proteins in the absence of any additional proteins, whereas others require the presence of ubiquitin-protein ligases (E3s). E3s are defined as proteins that participate with E1 and E2s in the ubiquitination of proteins, presumably by specifically binding to target proteins that are otherwise not recognized by E2s (Hershko and Ciechanover (1992) *Annu. Rev. Biochem.* 61, 761–807). Although only a few E3s have been described (Rolfe et al. (1995) *PNAS* 92:3264–3268; King et al. (1995) *Cell* 81:279–288; Reiss and Hershko (1990) *J. Biol. Chem.* 265, 3685–3690; Heller and Hershko (1990) *J. Biol. Chem.* 265, 6532–6535; and Bartel et al. (1990) *EMBO J.* 9, 3179–3189), the existence of a large group of proteins possessing E3-like activity is implied by the fact that selective protein degradation requires the specific targeting of may different proteins, often at particular stages of the cell cycle or differentiation.

The enzymatic reactions of the ubiquitin-dependent proteolytic pathway have been elucidated using damaged or artificial proteins. Only a few normal cellular targets of the ubiquitin system have been identified. These include plant phytocharome, the yeast transcription factor MAT α2, and cyclin B (Jabben et al. (1989) *J. Biol. Chem.* 264, 4998–5005; Hochstrasser et al. (1991) *Proc. Natl. Acad. Sci. USA* 88, 4606–4610; Glotzer et al.(1991) *Nature* 349, 132–138). The relevant E2s or E3s that are involved in the ubiquitination of these proteins have yet to be identified.

A novel mechanism of action for dominant oncogenes was postulated based on the observation that E6 protein of the human papillomavirus (HPV) types 16 and 18 could stimulate the ubiquitin-dependent degradation of the p53 tumor suppressor protein in vitro (Scheffner et al. (1990) *Cell* 63, 1129–1136).

Certain HPV types, such as HPV-16 and HPV-18, that infect the anogenital tract are associated with malignant lesions, most notably cervical cancer (for review see zur Hausen, (1991) *Virology* 184, 9–13). These types are referred to as high risk HPVs, as opposed to low risk anogenital-specific HPVs such as HPV-6 and HPV-11, which are generally associated only with benign lesions such as condyloma accuminata. Various cellular transformation assays have shown that the high risk HPVs encode two oncoproteins, E6 and E7. Significant to cervical carcinogenesis, both E6 and E7 are necessary and sufficient for efficient immortalization of human squamous epithelial cells, which are the natural host cells of these viruses (M ünger et al. (1989) *J. Virol.* 63, 4417–4421; Hawley-Nelson et al. (1989) *EMBO J.* 8, 3905–3910) and both of these genes are expressed in HPV-positive cervical cancers. Insight into the mechanisms by which E6 and E7 may contribute to cellular transformations has come from the recognition that, similar to the oncoproteins of other small DNA tumor viruses, E6 and E7 bind to cell regulatory proteins. Like the simian virus 40 large tumor antigen (SV40 T antigen) and the adenovirus 5 (Ad5) E1A proteins, E7 can bind to the product of the tumor suppressor gene RB (DeCaprio et al. (1988) *Cell* 54, 275–283; Whyte et al. (1988) *Nature* 334, 124–129; and Dyson et al. (1989) *Annu. Rev. Cell Biol.* 7, 25–69). The E6 protein, the SV40 T antigen, and the Ad5 E1B 55 kd protein are able to complex with wild-type p53 (Wemess et al. (1990) *Science* 248, 76–79; Lane and Crawford (1979) *Nature* 351, 453–456; Linzer and Levine (1979) *Cell* 17, 43–52; and Sarnow et al. (1982) *Cell* 28, 387–394). Mutations within the p53 gene, presumably inactivate the tumor suppressor function of wild-type p53 (Scheffner et al. (1991) *Proc. Natl. Acad. Sci. USA* 88, 5523–5527; Crook et al. (1991) *Oncogene* 6, 873–875; and Lin and Simmons (1990) *Virology* 176, 302–305). This is consistent with the hypothesis that complex formation with the viral oncoproteins interferes with the negative growth regulatory function of p53 and pRB. The mechanisms, however, by which the viral oncoproteins inactivate p53 seem to be quite different. The level and the half-life of p53 in SV40 and adenovirus-transformed cells are increased compared with uninfected cells (Oren et al. (1981) *Mol. Cell. Biol.* 1, 101–110; Recich et al. (1983) *Mol. Cell. Biol.* 3, 2143–2150), suggesting that SV40 T antigen and the Ad5 E1B 55 kd protein inactivate p53 by sequestering it into stable complexes. In contrast, the level and half-life of p53 in E6 immortalized cell lines or in HPV-positive cervical carcinoma cells are generally decreased (Scheffner et al. (1991) *Proc. Natl. Acad. Sci USA* 88, 5523–5527; Hubbert et al. (1992) *J. Virol.* 66, 6237–6241). This observation is consistent with the in vitro experiments showing that E6 stimulates the degradation of p53 via the ubiquitin-dependent proteolytic system (Scheffner et al. (1990) *Cell* 63, 1129–1136).

Attempts to study the binding of E6 to p53 in the absence of subsequent degradation revealed an additional cellular protein of an approximate molecular size of 100 kDa that participates in a complex with E6 (Huibregtse et al. (1991) *EMBO J.* 13, 4129–4135). This 100 kDa protein can interact with high risk HPV E6 proteins in the absence of p53, but not with p53 in the absence of E6 proteins, and was therefore termed E6-associated protein (E6AP). Recently, it has been report that the E6/E6AP complex, in concert with the ubiquitin-activating enzyme E1 and an E2, can mediate the ubiquitination of p53 in vitro (Scheffner et al. (1993) *Cell* 75, 495–505). This indicates that in this system the complex formed with E6, which can include E6AP, has the activity of a ubiquitin-protein ligase.

SUMMARY OF THE INVENTION

The present invention relates to the discovery that antisense nucleic acids complimentary to regions of an E6AP gene can be used to regulate cellular p53 levels.

In general the invention features E6AP antisense constructs which, by inhibiting expression of the E6AP gene product, can modulate cellular p53 levels in p53+ epithelial cells. By manipulation (e.g., activation) of this cell-cycle checkpoint, proliferation or other mitotic and/or transcriptional activity of a cell can be modulated by the subject antisense constructs. Accordingly, the compositions of the present invention can be used to regulate cell proliferation and/or viability in both cell cultures and in animals. The E6AP antisense constructs can be used to modulate proliferation of ectodermally-derived tissue/cells, such as epithelial cells. For instance, the present invention provides methods for treating papillomavirus (PV) infected cells, including PV-transformed cells. Furthermore, the subject compositions can be used to regulate proliferation of epithelial tissues, both transformed and non-transformed, such as in wound repair processes, proliferative skin disorders, and protection against cytotoxic agents.

In a preferred embodiment, the invention features an antisense nucleic acid which specifically hybridizes to an E6AP gene. Preferably, the nucleic acid is at least about 10 nucleotides long, though more preferably 15, 20, 30, 40 or 50 nucleotides in length.

In an exemplary embodiment, the antisense molecule is generated ex vivo, e.g. by chemical synthesis rather than biochemical synthesis. Accordingly, in certain embodiments the nucleic acid is a nonhydrolyzable DNA analog. Exemplary antisense constructs of this form include at least a portion of nucleotide sequence which specifically hybridizes to SEQ ID No: 1. For example, the nucleic acid preferably comprises a nucleotide sequence complementary to at least about 20 nucleotides from nucleotides 1–139, nucleotides 1100–1325, or nucleotides 2100–2316 of SEQ ID No: 1.

In another embodiment, the complementary nucleic acid (e.g., the antisense agent) is generated biochemically by expression of a gene construct transfected into the target cell. Accordingly, the invention features a recombinant gene construct comprising a gene expressible as a nucleic acid complementary to an E6AP gene. Exemplary gene constructs comprise an expressible gene which can be transcribed to produce a nucleic acid which specifically hybridizes to the nucleic acid sequence designated by SEQ ID No: 1. The nucleic acid preferably comprises a nucleotide sequence complementary to at least 20 nucleotides from nucleotides 1–139, nucleotides 1100–1325, or nucleotides 2100–2316 of SEQ ID No: 1. Preferably, the nucleic acid transcribed from the gene construct comprises nucleotide sequence complementary to at least about 10 nucleotides of an E6AP gene, though more preferably 15, 20, 30, 40 or 50 nucleotides.

In still a further embodiment, the invention features a pharmaceutical composition comprising an antisense nucleic acid which specifically hybridizes to an E6AP gene, which nucleic acid is present in a pharmaceutically acceptable carrier. In a preferred embodiment, the pharmaceutical preparation is a cosmetic preparation for topical application, especially cutaneous application.

In another preferred embodiment, the invention features a pharmaceutical composition comprising a gene construct including a gene expressible as a nucleic acid complimentary to an E6AP gene, which nucleic acid is present in a pharmaceutically acceptable carrier. In a preferred embodiment, the pharmaceutical preparation is a cosmetic preparation for topical application, especially cutaneous application.

In yet another preferred embodiment, the invention features an E6AP antisense nucleic acid represented in any of SEQ ID No: 2, SEQ ID No: 4 or SEQ ID No: 6.

In one aspect, the invention features a method of regulating a cellular p53 level comprising: introducing into a cell, e.g., a normal or a p53+ transformed cell, an E6AP antisense construct in an amount sufficient to produce a population of nucleic acids of which at least a portion is complimentary to an E6AP gene, which nucleic acids inhibit expression of the E6AP gene. Inhibition of the E6AP gene results in a statistically significant increase in the cellular p53 level. Exemplary, E6AP antisense constructs comprise a nucleic acid complimentary to an E6AP gene. Preferably, the complementary portion of the nucleic acid is at least 10 nucleotides long, more preferably at least 20, 30, 40 or 50 nucleotides in length.

Preferably, the nucleic acid is a nonhydrolyzable DNA analog. Another exemplary E6AP construct is a gene construct comprising a gene expressible as a nucleic acid of which at least a portion is complimentary to an E6AP gene.

For example, the invention features a method of treating papillomavirus (PV), e.g., human papillomavirus (HPV), e.g., high risk HPV, e.g., HPV-16, -18, -31 or -33, induced conditions comprising: administering to an animal infected with the virus the E6AP antisense construct of the present invention in an amount sufficient to modulate a p53 level in cells infected with the PV, wherein the treatment results in amelioration of a PV induced condition, e.g. inhibits proliferation of the PV-infected cells.

In yet another embodiment, the invention features a method of regulating proliferation of an epithelial cell, comprising: contacting the cell with an E6AP antisense construct of the present invention in an amount sufficient to produce a population of nucleic acids complimentary to an E6AP gene, which nucleic acids inhibit expression of the E6AP gene. Inhibition of the E6AP gene resulting in the regulation of cell proliferation and/or cell viability.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., New York); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims.

DETAILED DESCRIPTION OF THE DRAWINGS

DETAILED DESCRIPTION OF THE INVENTION

The p53 gene is a known tumor-suppressing gene (Green (1989) *Cell* 56:1–3; Mowat et al (1985 *Nature* 314:633–636). The protein encoded by the p53 gene is a nuclear protein that forms a stable complex with both the SV40 large T antigen and the adenovirus E1B 55 kd protein. The p53 gene product may be inactivated by binding to these proteins. Many lines of evidence point to the importance of p53 in human carcinogenesis. For instance, mutations within the p53 gene are the most frequent genetic aberration thus far associated with human cancer. Emerging evidence suggests that p53 is a checkpoint protein that plays an important role in sensing DNA damage or regulating cellular response to stress.

Under normal conditions, p53 is an unstable protein and is present at very low levels in the cell. The level of p53 in a cell appears to be controlled at least in party by degradation involving the ubiquitin system. Treating cells with UV light or X rays dramatically reduces the rate of p53 degradation, leading to a rapid increase in its concentration in the cell and presumably inducing the transcription of genes that block passage through the restriction point. However, while normal cell lines irradiated in G1 fail to enter S phase, many tumor lines do not. In fact, there is a perfect correlation between cell lines that lack this feedback control and cells that have mutations in the p53 gene. These mutations are of two sorts: recessive mutations that inactivate the gene, and dominant mutations that produce abnormal proteins.

The present invention derives from the discovery that antisense nucleic acids against the E6AP message can, by apparently disrupting E6AP expression, cause marked increases in the cellular p53 levels. The upregulation of p53, in turn, can cause inhibition of cell proliferation or growth, e.g. can induce quiescence, or can result in cell death, such as by apoptotic mechanisms. Consequently, the E6AP antisense constructs of the present invention can be used to modulate the function of p53 in order to control of cellular proliferation and/or viability. For example, as described below, the E6AP antisense constructs of the present invention can be used to inhibit proliferation of PV-infected and PV-transformed cells. Furthermore, the anti-proliferative activity of the subject antisense constructs may also be employed in the treatment of other hyperplasias or neoplasias which arise in p53+ cell populations which contain wild-type p53 (e.g. may function to induce apoptosis), or mutant p53 (e.g., function to offset a diminishment in p53 activity by increasing the level of mutant p53). Moreover, such antisense constructs can also be used prophylactically to increase p53 levels and thereby enhance protection against DNA damaging agents (e.g., radiation) or other cytotoxic agents whenever it is known that exposure to such damaging agents is imminent. For example, the therapy described below can be used to protect normal cells from cytotoxic agents administered in the chemotherapeutic treatment of a tumor having a p53⁻ phenotype.

Accordingly, the present invention provides compositions and methods for modulating proliferation of cells by controlling E6AP dependent levels of p53. In general, the levels of p53 can be regulated by controlling E6AP levels through the use of the antisense constructs of the present invention. It will be apparent from the following discussion that the subject pharmaceutical preparations and methods can be utilized for controlling the proliferation of tissue, such as epithelial-derived tissue, as in the treatment of disorders marked by aberrant proliferation, or in the repair of damaged tissue. For example, the subject method can be used in the treatment of disorders, or surgical or cosmetic repair of such epithelial tissues as skin and skin organs; corneal, lens and other ocular tissue; mucosal membranes; and periodontal epithelium. For instance, the methods and compositions disclosed herein provide for the treatment or prevention of a variety of damaged epithelial and mucosal tissues, particularly those resulting from hyperplastic or neoplastic conditions, especially those having a papillomavirus as a causative agent. For instance, it will be evident that the method will find ready application for the treatment or prophylaxis of, for example, psoriasis; keratosis; acne; comedogenic lesions; verrucous lesions such as verruca plana, plantar warts, verruca acuminata, and other verruciform lesions marked by proliferation of epithelial cells; folliculitis and pseudofolliculitis; keratoacanthoma; callosities; Darier's disease; ichthyosis; lichen planus; molluscous contagiosum; melasma; Fordyce disease; and keloids or hypertrophic scars. E6AP antisense formulations of the present invention may also be used as part of treatment regimens in auto-immune diseases for affecting healing of proliferative manifestations of the disorder, as for example, part of a treatment for aphthous ulcers, pemphigus such as pemphigus vulgaris, pemphigus foliaceus, pemphigus vegetans or pemphigus erythematous, epidermolysis, lupus lesions or desquamative lesions.

Furthermore, the subject method can be used to control wound healing processes, as for example may be desirable in connection with any surgery involving epithelial tissue, such as from dermatological or periodontal surgeries. Exemplary surgical repair for which E6AP antisense therapy is a candidate treatment include severe burn and skin regeneration, skin grafts, pressure sores, diabetic ulcers, fissures, post surgery scar reduction, and ulcerative colitis.

The subject method can also be employed to cause inhibition of hair growth, as for example, a way of reducing the growth of human hair as opposed to its conventional removal by cutting, shaving, or depilation, e.g. in the treatment of trichosis, as well as to protect hair follicle cells from radiation-induced death during cytotoxic therapies.

In preferred embodiments the E6AP antisense construct of the present invention is preferably capable of: suppressing tumor growth, e.g., in a tumor cell in which endogenous E6AP is involved in p53 regulation; suppressing growth of papillomavirus-infected cells, e.g., HPV-infected cells; inhibiting growth of a papillomavirus-infected cell, e.g., an HPV-infected cell, e.g., a high-risk HPV infected cell, e.g., and HPV-16, -18, -31, or -33 infected cell, e.g., a bovine papillomavirus (BPV)-infected cell; inhibiting infection of a cell by a papillomavirus, e.g., an HPV, e.g., ahigh-risk HPV, e.g., and HPV-16, -18, -31, or -33, e.g., a bovine papillomavirus (BPV); inhibiting transformation of a cell by a papillomavirus, e.g., an HPV, e.g., a high-risk HPV, e.g., and HPV-16, -18, -31, or -33, e.g., a bovine papillomavirus; or inhibiting immortalization of a cell, e.g., a human cell, by a papillomavirus, e.g., an HPV, e.g., a high-risk HPV, e.g., and HPV-16, -18, -31, or -33, e.g., a bovine papillomavirus; inhibiting the growth of, or diminishing the size of a wart.

For instance, contacting cells with antisense constructs that alter the E6AP levels can inhibit pathological progression of papillomavirus infection, such as preventing or reversing the formation of warts, e.g. Plantar warts (verruca plantaris), common warts (verruca plana), Butcher's common warts, flat warts, genital warts (condyloma acuminatum), or epidermodysplasia verruciformis; as well as treating papillomavirus cells which have become, or are at risk of becoming, transformed and/or immortalized, e.g. cancerous, e.g. a laryngeal papilloma, a focal epithelial, a cervical carcinoma.

In another preferred embodiment, the E6AP antisense construct of the present invention is preferably capable of regulating a p53 level in either of normal epithelial cells or p53+ transformed epithelial cells. For instance, contacting the cell with an E6AP antisense construct in an amount sufficient to produce a population of nucleic acids complimentary to an E6AP gene, will result in inhibition of the E6AP gene expression, leading to a statistically significant increase in the cellular p53 level. In the case of a normal cell, increase in cellular p53 level will result in cells arresting in G1 phase and impeded progression into S phase, thus making cells quiescent. This can be extremely important in cases where the cells need to be protected from DNA damaging agents, e.g., radiation. In one exemplary embodiment, an E6AP antisense construct of the present invention can be used via topical administration to prevent radiation induced death of epithelial cells, i.e., prevent hair follicle death in patients undergoing chemotherapy, by arresting cells in G1 phase and protecting them from damage. In the case of a p53+ transformed cell, an increase in a cellular p53 level will result in inhibition of proliferation, i.e., can induce apoptosis, e.g., programmed cell death. The anti-proliferative activity of such antisense construct can be employed in the treatment of many different cellular transformations, e.g., hyperplasias or neoplasias.

For convenience, certain terms employed in the specification, examples, and appended claims are collected here.

As used herein, the term "specifically hybridizes" refers to the ability of antisense constructs of the present invention to bind under cellular conditions, e.g., physiological conditions present in a given cell, with the cellular mRNA and/or genomic DNA encoding a E6AP gene so as to inhibit expression of that protein, e.g. by inhibiting transcription and/or translation. Such hybridization should be selective to the E6AP gene, e.g., resulting in hybridization to non-E6AP genes, under cellular conditions, at a level of less than 25% relative to hybridization to the E6AP gene, more preferably less than 10% and even more preferably less than 5%. For instance, antisense constructs of the present invention are preferably at least 50% homologous to the nucleotide sequence encoding an E6AP gene, more preferably at least 70% homologous to the nucleotide sequence encoding an E6AP gene and most preferably at least 90% homologous to the nucleotide sequence encoding an E6AP gene. Of course, antisense constructs identical to the complementary strand of SEQ ID No. 1 are more preferred.

As used herein the term "suppressing tumor growth" refers to the E6AP antisense construct's ability to, by regulating cellular p53 levels, inhibit proliferation of p53+ transformed cells, e.g., to cause apoptosis of certain p53+ transformed cells.

As used herein, the term "gene" or "recombinant gene" refers to a nucleic acid including an open reading frame encoding an E6AP, including both exon and (optionally) intron sequences, as well as 5' and 3' untranslated sequences. Exemplary E6AP coding sequence is represented by SEQ ID No:1. The term "intron" refers to a DNA sequence present in a given E6AP gene which is not translated into protein and is generally found between exons. The term "gene", as used herein, further refers to a mRNA which encodes an E6AP protein.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides as well as nonhydrolyzable DNA analogs, e.g., phosphoramidate, phosphothioate and methylphosphonate analogs of DNA.

As used herein, the term "transfection" means the introduction of a nucleic acid, e.g., an expression vector, into a recipient cell by nucleic acid-mediated gene transfer.

As used herein, "proliferating" and "proliferation" refer to cells undergoing mitosis.

As used herein, "transformed cells" is art recognized and refers to cells which have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control. In general, term "transformed cell" refers to cells which exhibit at least the following properties: (i) increased capacity to persist in serial subcultures; (ii) increased growth rate in vitro, and (iii) loss of contact inhibition.

The term "immortal cell" or "immortalized cell" is art recognized, and is used to refer to transformed cells which are able to persist in serial subcultures indefinitely.

The term "normal cell" is art recognized and refers to cells that are not transformed. Preferably, normal cells do not have increased capacity to persist in serial subcultures or increased growth rate in vitro. Normal cells when grown in cultures do not exhibit loss of contact inhibition.

The term "p53+" refers to a cell in which express of p53, or mutants thereof, occurs, though it will be understood that the half-life of the protein can vary greatly. This is in contrast to "p53–" cells in which expression of the p53 gene has been disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

As used herein the term "animal" refers to mammals, preferably mammals such as live stock or humans. Likewise, a "patient" or "subject" to be treated by the subject method can mean either a human or non-human animal.

As used herein the term "E6AP antisense construct" refers to both the ex vivo generated oligonucleotide and the gene therapy constructs described herein.

The term "ectoderm" refers to the outermost of the three primitive germ layers of the embryo; from it are derived the epidermis and epidermal tissues such as the nails, hair and glands of the skin, the nervous system, external sense organs and mucous membrane of the mouth and anus.

The terms "epithelia" and "epithelium" refer to the cellular covering of internal and external body surfaces (cutaneous, mucous and serous), including the glands and other structures derived therefrom, e.g., corneal, esophegeal, epidermal, and hair follicle epithelial cells. Other exemplary epithelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, which that characteristically found lining hollow organs that are subject to great mechanical change due to contraction and distention, e.g. tissue which represents a transition between stratified squamous and columnar epithelium. The term "epithelialization" refers to healing by the growth of epithelial tissue over a denuded surface.

Furthermore, the term "epithelioid cells" refers to cells which have phenotypes resembling epithelial cells. For instance, epithelioid cells can be cells from an epithelioma or other epitheliomatous cells, e.g. any tumor derived from epithelium, such as a carcinoma.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Another carcinomatous epithelial growth is "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "epidermis" refers to the outermost and nonvascular layer of the skin, derived from the embryonic ectoderm, varying in thickness from 0.07–1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, conified non-nucleated cells. In the epidermis of the general body surface, the clear layer is usually absent. An "epidermoid" is a cell or tissue resembling the epidermis, but may also be used to refer to any tumor occurring in a noncutaneous site and formed by inclusion of epidermal elements.

The term "hair" (or "pilus") refers to a threadlike structure, especially the specialized epidermal structure composed of keratin and developing from a papilla sunk in the corium, produced only by mammals and characteristic of that group of animals. Also, the aggregate of such hairs. A "hair follicle" refers to one of the tubular-invaginations of the epidermis enclosing the hairs, and from which the hairs grow; and "hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis, such as "epidermodysplasia verruciformis", which is a condition due to a virus identical with or closely related to the virus of common warts. Another example is "epidermolysis", which refers to a loosened state of the epidermis with formation of blebs and bullae either spontaneously or at the site of trauma.

As used herein, the term "psoriasis" refers to a hyperproliferative skin disorder which alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

The term "cosmetic preparation" refers to a form of a pharmaceutical preparation which is formulated for topical administration.

An "effective amount" of an E6AP antisense construct, with respect to the subject method of treatment, refers to an amount of the construct in a preparation which, when applied as part of a desired dosage regimen, provides inhibition of cell proliferation or causes loss of viability so as to reduce or cure a proliferative disorder according to clinically acceptable standards.

One aspect of the invention relates to the use of the isolated nucleic acid in "antisense" therapy. As used herein, "antisense" therapy refers to administration or in situ generation of oligonucleotide probes or their derivatives which specifically hybridizes (e.g. binds) under cellular conditions, with the cellular mRNA and/or genomic DNA encoding a E6AP so as to inhibit expression of that protein, e.g. by inhibiting transcription and/or translation. The binding may be by conventional base pair complementarity, or, for example, in the case of binding to DNA duplexes, through specific interactions in the major groove of the double helix. Preferably, the oligonucleotide probes of the present invention are at least 20–50 nucleotides long, more preferably at least 20–30 nucleotides long and most preferably at least 25–26 nucleotides long. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes an E6AP. Alternatively, the antisense construct is an oligonucleotide probe which is generated ex vivo and which, when introduced into the cell causes inhibition of expression by hybridizing with the mRNA and/or genomic sequences encoding E6AP. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

In therapeutic application, the ex vivo derived oligomers are utilized in a manner appropriate for antisense therapy in general. For such therapy, the oligomers of the invention can be formulated for a variety of modes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneuos for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, particularly cosmetic formulations, the oligomers of the invention are formulated into ointments, salves, gels, or creams as generally known in the art.

In another embodiment, the antisense nucleic acids are provided by use of an "expression" constructs, which can be transcribed in a cell to produce the antisense nucleic acid. Such expression constructs may be administered in any biologically effective carrier, e.g. any formulation or composition capable of effectively transfecting cells either in vitro or in vivo with an E6AP antisense construct. Approaches include insertion of the antisense nucleic acid in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject proteins into a cell is by use of a viral vector containing nucleic acid, e.g. an antisense nucleic acid. Infection of cells with a viral vector has the advantage that a large proportion of the targeted cells can receive the nucleic acid. Additionally, antisense constructs encoded within the viral vector, e.g., by a nucleic acid contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the antisense E6AP constructs, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J. Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for the subject E6AP antisense constructs, it is important to note that a prerequisite for the successful infection of target cells by most retroviruses, and therefore of stable introduction of the antisense E6AP construct, is that the target cells must be dividing. In general, this requirement will not be a hindrance to use of retroviral vectors to deliver E6AP antisense constructs. In fact, such limitation on infection can be beneficial in circumstances wherein the tissue (e.g. non-transformed cells) surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) PNAS 86:9079–9083; Julan et al. (1992) J. Gen Virol 73:3251–3255; and Goud et al. (1983) Virology 163:251–254); or coupling cell surface ligands to the viral env proteins (Neda et al. (1991) J Biol Chem 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences which control expression of the E6AP antisense nucleic acid of the retroviral vector.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al. (1988) BioTechniques 6:616; Rosenfeld et al. (1991) Science 252:431–434; and Rosenfeld et al. (1992) Cell 68:143–155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al. (1992) cited supra), endothelial cells (Lemarchand et al. (1992) Proc. Natl. Acad. Sci. USA 89:6482–6486), hepatocytes (Herz and Gerard (1993) Proc. Natl. Acad. Sci. USA 90:2812–2816) and muscle cells (Quantin et al. (1992) Proc. Natl. Acad. Sci. USA 89:2581–2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) Cell 16:683; Berkner et al., supra; and Graham et al. in Methods in Molecular Biology, E. J. Murray, Ed. (Humana, Clifton, N.J., 1991) vol. 7. pp. 109–127). Expression of the inserted E6AP antisense construct can be under control of, for example, the E1A promoter, the major late promoter (MLP) and associated leader sequences, the E3 promoter, or exogenously added promoter sequences.

Yet another viral vector system useful for delivery of the subject E6AP antisense constructs is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97–129). It is also one of the few viruses that may integrate its DNA into non-dividing cells, and exhibits a high frequency of stable integration (see for example Flotte et al. (1992) Am. J. Respir. Cell. Mol. Biol. 7:349–356; Samulski et al. (1989) J. Virol. 63:3822–3828; and McLaughlin et al. (1989) J. Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J. Virol. 51:611–619; and Flotte et al. (1993) J. Biol. Chem. 268:3781–3790).

Other viral vector systems that may have application in gene therapy have been derived from herpes virus, vaccinia virus, and several RNA viruses.

In addition to viral transfer methods, such as those illustrated above, non-viral methods can also be employed to cause expression of an E6AP antisense construct in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject E6AP antisense constructs by the targeted cell. Exemplary gene delivery systems of this type include liposomal derived systems, polylysine conjugates, and artificial viral envelopes.

In a representative embodiment, an E6AP antisense construct can be entrapped in liposomes bearing positive charges on their surface (e.g., lipofectins) and (optionally) which are tagged with antibodies against cell surface antigens of the target tissue (Mizuno et al. (1992) No Shinkei Geka 20:547–551; PCT publication WO91/06309; Japanese patent application 1047381; and European patent publication EP-A-43075). For example, lipofection of papilloma-infected cells can be carried out using liposomes tagged with monoclonal antibodies against PV-associated antigen (see, Viac et al. (1978) J Invest Dermatol 70:263–266; see also Mizuno et al. (1992) Neurol. Med. Chir. 32:873–876).

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, the subject E6AP antisense construct can be used to transfect hepatocytic cells in vivo using a soluble polynucleotide carrier comprising an asialoglycoprotein conjugated to a polycation, e.g. poly-lysine (see U.S. Pat. No. 5,166,320). It will also be appreciated that effective delivery of the subject nucleic acid constructs via-mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al. (1993) Science 260–926; Wagner et al. (1992) PNAS 89:7934; and Christiano et al. (1993) PNAS 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057).

Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. Various slow release polymeric devices have been developed and tested in vivo in recent years for the controlled delivery of drugs, including proteinacious biopharmaceuticals, and can be adapted for release of viral particles through the manipulation of the polymer composition and form. A variety of biocompatible polymers (including hydrogels), including both biodegradable and non-degradable polymers, can be used to form an implant for the sustained release of an the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, Concise Encyclopedia of Medical & Dental Materials, ed. by David Williams (MIT Press: Cambridge, Mass., 1990); and the Sabel et al. U.S. Pat. No. 4,883,666. In another embodiment of an implant, a source of cells producing a the recombinant virus is encapsulated in implantable hollow fibers. Such fibers can be pre-spun and subsequently loaded with the viral source (Aebischer et al. U.S. Pat. No. 4,892,538; Aebischer et al. U.S. Pat. No. 5,106,627; Hoffman et al. (1990) Expt. Neurobiol. 110:39–44; Jaeger et al. (1990) Prog. Brain Res. 82:41–46; and Aebischer et al. (1991) J. Biomech. Eng. 113:178–183), or can be co-extruded with a polymer which acts to form a polymeric coat about the viral packaging cells (Lim U.S. Pat. No. 4,391,909; Sefton U.S. Pat. No. 4,353,888; Sugamori et al. (1989) Trans. Am. Artif. Intern. Organs 35:791–799; Sefton et al. (1987) Biotechnol. Bioeng. 29:1135–1143; and Aebischer et al. (1991) Biomaterials 12:50–55). Again, manipulation of the polymer can be carried out to provide for optimal release of viral particles.

Another aspect of the present invention provides a method for treating an animal having unwanted cell growth characterized by a loss of wild-type function of p53 by an E6AP dependent mechanism, e.g., such as by infection with a papillomavirus. In general, the method comprises administering a therapeutically effective amount of an E6AP antisense construct to inhibit the interaction of the E6AP protein with p53 (or other cellular or viral proteins).

For instance, E6AP antisense preparations of the present invention can be used for the treatment of cutaneous proliferations that are benign or malignant, which are either of viral origin such as common warts, plane warts or epidermodysplasic verrucifomr, or which are a result of other cellular transforming and/or immortalizing events, such as may be induced by radiation.

Warts are known to be intra-epidermal tumors of the skin caused by infection with virsues such as papillomaviruses. Papillomaviruses (PV) have been linked to widespread, serious human diseases, especially carcinomas of the genital and oral mucosa. Papillomaviruses can induce benign, dysplastic and malignant hyperproliferations of skin and mucosal epithelium (see, for example, Mansur and Androphy, (1993) Biochim Biophys Acta 1155:323–345; Pfister (1984) Rev. Physiol. Biochem. Pharmacol. 99:111–181; and Broker et al. (1986) Cancer Cells 4:17–36, for reviews of the molecular, cellular, and clinical aspects of the papillomaviruses). The human papillomaviruses (HPV) are a heterogeneous group of DNA tumor viruses associated with hyperplastic (warts, condylomata), pre-malignant and malignant lesions (carcinomas) of squamous epithelium.

Tens of millions of women suffer from HPV infection of the genital tract. Significant number of these women eventually develop cancer of the cervix. It has been estimated that perhaps twenty percent (20%) of all cancer deaths in women worldwide are from cancers which are associated with HPV, and as many as 90% of all cervical cancer maybe linked to HPV. In light of the present invention, proliferation of PV-infected cells, especially PV-transformed cells, can be inhibited by a treatment protocol which includes administration of the subject E6AP antisense compositions.

The subject compositions can also be used in the treatment of other epithelial proliferative disorders caused by wart viruses. For example, bowenoid papulosus is a tumor of the genitalia induced by premalignant wart viruses and usually afflicting men. Condylomatous dysplasia and cervical carcinoma in situ are premalignant tumors of the female genitalia, also induced by wart viruses. Known treatments for all three of these tumors include cryosurgery, 5-fluorouracil, trichloroacetic acid, podophyllin and interferon. These treatments are painful, however, and not always effective. According to the present invention, such therapies can be augmented or replaced by treatment with the subject E6AP antisense preparations.

In yet another embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of an E6AP antisense construct can be used to treat varying forms of psoriasis, be they cutaneous, mucosal or ungual. Psoriasis, as described above, is typically characterized by epidermal keratinocytes which display marked proliferative activation and differentiation along a "regenerative" pathway. Treatment with the E6AP antisense therapeutics of the present invention can be used to reverse the pathological epidermal activiation and can provide a basis for sustained remission of the disease.

A variety of other keratotic lesions are also candidates for treatment with the subject antisense preparations. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of E6AP antisense compositions in amounts sufficient to inhibit hyperproliferation of epidermal/epidermoid cells of the lesion.

Another cutaneous disorder of interest, rosacea, is an inflammatory disease due to abnormal sensitivity of the vasculature. Rosacea often results in secondary sebaceous gland hyperplasia and inflammation producing characteristic skin lesions. Prior art treatments for rosacea have generally involved the use of antiinflammatory antibiotics such as metronidizole. The present invention contemplates a therapeutic regimen for rosacea which includes E6AP antisense treatment to inhibit hyperplasia, particularly of glandular epithelial cells.

Acne represents yet another dermatologic ailment which may be treated with the subject E6AP antisense constructs. Acne vulgaris, for instance, is a multifactorial disease most commonly occurring in teenagers and young adults, and is characterized by the appearance of inflammatory and non-inflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by Propinobacterium acnes and *Staphylococcus epidermidis* bacteria and *Pitrosporum ovale*, a yeast. Treatment with E6AP antisense nucleic acid, particularly delivered in a topical preparation, may be useful for preventing the transitional features of the ducts, e.g. hypercornification, which lead to lesion formation. The antisense treatment may further include, for example, antibiotics, retinoids and anti-androgens The present invention also provides a method for treating various forms of dermatitis. Dermatitis is a descriptive term referring to poorly demarcated lesions which are either pruritic, erythematous, scaley, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of diy scales stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, antisense preparations can be used in the treatment and/or prevention of certain symptoms of dermatitis caused by unwanted proliferation of epithelial cells. Such E6AP antisense therapies for these various forms of dermatitis can also include topical and systemic corticosteroids, antipuritics, and antibiotics.

Also included in ailments which may be treated with the subject E6AP antisense compositions are disorders specific to non-humans, such as mange.

Yet another aspect of the present invention relates to the use of the subject E6AP antisense preparations to control hair growth. The growth of hard keratin fibers such as wool and hair is dependent on the proliferation of dermal sheath cells. Hair follicle stem cells of the sheath are highly active, and give rise to hair fibers through rapid proliferation and complex differentiation. The hair cycle involves three distinct phases: anagen (growing), catagen (regressing), and telogen (resting). The epidermal stem cells of the hair follicle are activated by dermal papilla during late telogen. This is termed "bulge activation". Moreover, such stem cells are thought to be pluripotent stem cells, giving rise not only to hair and hair follicle structures, but also the sebaceous gland and epidermis. As described in the appended examples, the subject method provides a means for altering the dynamics of the hair growth cycle to induce quiescence of proliferation of hair follicle cells, particularly stem cells of the hair follicle.

For instance, E6AP antisense treatments can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, a preparation of an E6AP antisense construct can be used to manage hirsutism, a disorder marked by abnormal hairiness. E6AP antisense therapy can also provide a process for extending the duration of depilation.

Moreover, because p53 upregulation is presumably cytostatic to epithelial cells, rather than cytotoxic, it can be used to protect hair follicle cells from cytotoxic agents which require progression into S-phase of the cell-cycle for efficacy, e.g. radiation-induced death. Treatment with one of the subject antisense preparations provides protection by causing the hair follicle cells to become quiescent, e.g., by inhibiting the cells from entering S phase, and thereby preventing the follicle cells from undergoing mitotic catastrophe or programmed cell death. For instance, E6AP antisense treatments can be used for patients undergoing chemo- or radiation-therapies which ordinarily result in hair loss. By inhibiting cell-cycle progression during such therapies, the subject antisense treatment can protect hair follicle cells from death which might otherwise result from activation of cell death programs. After the therapy has concluded, antisense treatment can also be removed with concommitant relief of the inhibition of follicle cell proliferation.

Furthermore, it will be understood that the subject E6AP antisense preparations can be used to treat anomalies resulting from proliferation of tracheobronchial and nasal epithelial cells. For instance, an E6AP antisense therapy can be used to prevent growth of tracheaobronchial tumors. Likewise, trachael stenosis resulting from squamous metaplasia of the mucosal columnar epithelial can be controlled with the subject antisense therapy.

Yet another aspect of the present method concerns the use of E6AP antisense preparations for controlling tissue repair after surgery and remodelling following injury. In one embodiment, the subject antisense preparations can be used to help control guided tissue regeneration, such as when used in conjunction with bioresorptable materials. For example, incorporation of periodontal implants, such as prosthetic teeth, can be facilitated by treatment with the subject E6AP antisense molecules. Reattachment of a tooth involves both formation of connective tissue fibers and re-epithelization of the tooth pocket. E6AP antisense treatment can be used to accelerate connective tissue reattachment by inhibiting the mitotic function of basal epithelial cells in early stages of wound healing.

Furthermore, the subject antisense molecules can be used to attenuate cosmetic damage by providing more particular control over proliferation of epidermal cells such that keloidal scarring can be avoided during connective tissue repair, including dermatoplasty. In similar fashion, E6AP antisense preparations can be used to control the rate of proliferation of epithelial cells during other plastic surgery procedures, including proctoplasty and rhinoplasty.

Those of skill in treating disorders which are amenable to regulation by the subject E6AP antisense constructs can determine the effective amount of a particular antisense construct to be formulated in a pharmaceutical or cosmetic preparation. In general it is contemplated than an effective amount would be from 0.001 mg/kg to 50 mg/kg body weight and more preferably from 0.01 mg/kg to 10 mg/kg body weight.

In addition, the subject E6AP antisense constructs can be used as an additive for cultured cells, such as for maintaining the integrity of a culture of differentiated cells. To illustrate, in vitro cutaneous culture systems have proved to be fundamental and indispensable tools for the study of skin development and repair, as well as for the identification of trophic factors. Differentiated epithelial cells sought to be maintained in the culture are "post-mitotic" and therefore not affected by the use of anti-mitotic agents, such as the subject E6AP antisense constructs. In contrast, other cells harvested with the differentiated neuronal cells, such as fibroblasts, are typically mitotic, e.g., capable of proliferating in the culture. Moreover, terminally-differentiated cells can also lose their differentiated state over time in culture and become mitotic. This is commonly observed when they are grown in culture from adult tissue. Accordingly, the subject E6AP antisense constructs can be provided in the cell culture as anti-mitotic agents in order to provide a means for maintaining the integrity of the culture with respect to the differentiated cells. See, for example, Kari et al. (1985) *Brain Res* 339:1–7; Wood, PM (1976) *Brain Res* 115:361–375; or Wrathall et al. (1981) *Brain Res* 229:163–181.

EXEMPLIFICATION

The invention, now being generally described, will be more readily understood by reference to the following examples, which are included merely for purposes of illustration of certain aspects and embodiments of the present invention and are not intended to limit the invention.

Construction of Antisense Oligonucleotides

Oligonucleotides (25–26 mers) complimentary to the target E6AP sequence (mRNA or genomic) were synthesized using standard techniques (Van der Krol et al. (1988) *Biotechniques* 6:958–976; and Stein et al. (1988) *Cancer Res* 48:2659–2668). In order for synthesized oligonucleotides to be stable in vivo, modified oligonucleotide which are resistant to endogenous nucleases, e.g. exonucleases and/or endonucleases, should be constructed. For these experiments, phosphothioate analogs of DNA were synthesized. Several considerations should be taken into account when constructing antisense oligonucleotides for the use in the methods of the invention: (1) oligos should have a GC content of 50% or more; (2) avoid sequences with stretches of 3 or more G's; and (3) oligonucleotides should not be longer than 25–26 mers. For each antisense oligonucleotide used in the transfection experiments described below, a mismatched control was constructed. The controls were generated by reversing the sequence order of the corresponding antisense oligonucleotide in order to conserve the same ratio of bases. Antisense oligonucleotides and their respective controls are represented in Table 1.

TABLE 1

Antisense Oligonucleotides for E6AP

| OLIGO NAME | SEQUENCE (5'-3') | % GC | SEQ ID No: |
| --- | --- | --- | --- |
| AS4 | CGGCTAGCTTCAATGTCGTCAGACTG | 54% | SEQ ID No: 2 |
| AS5(c) | GCTAGACTGCTGTAACTTCGATCGGC | reverse of AS4 | SEQ ID No: 3 |
| AS6 | GAAGTGTCAGCTCGCTGGACTCAGG | 60% | SEQ ID No: 4 |
| AS7(c) | GGACTCAGGTCGCTCGACTGTGAAG | reverse of AS6 | SEQ ID No: 5 |
| AS8 | CCATATGAAAACCTCTCCGAAAAGCC | 46% | SEQ ID No: 6 |

TABLE 1-continued

Antisense Oligonucleotides for E6AP

| OLIGO NAME | SEQUENCE (5'–3') | % GC | SEQ ID No: |
|---|---|---|---|
| AS9(c) | CCGAAAAGCCTCTCCAAAAGTATACC | reverse of AS8 | SEQ ID No: 7 |

HeLa Cell Transfections

Opti-MEM, serum fee media was purchased from Gibco-BRL. Lipofectin is 1:1 mixture of the cationic lipid DOTMA and the neutral lipid DOPE, also purchased from Gibco-BRL.

HeLa cells were grown to 40–80% confluence and washed twice with PBS (containing no $Mg^{++}$ or $Ca^{++}$). 24 ml of Opti-MEM media was mixed with 160 $\mu$l of lipofectin. (Lipofectin is 750 $\mu$M of cationic lipid (one positive charge each). The preferred charge ratio is 1:1. Because each 25 mer oligonucleotide has 25 negative charges, 5 $\mu$M of cationic lipid are needed to complex at a 1:1 charge ratio with 200 nM concentration of oligonucleotide.) 2 ml of Opti-MEM/lipofectin solution was then added to the cells per well, followed by the addition of 2 $\mu$l of 200 $\mu$M stock of respective AS oligonucleotide to each well for a final AS oligo concentration of 200 nM. Cells were incubated at 37° C. for 5 hours and washed twice gently with PBS. DMEM complete growth media was added to the cells and they were grown 24 and 48 hours respectively before harvesting cells for lysis.

Western Blot

Figure 1:
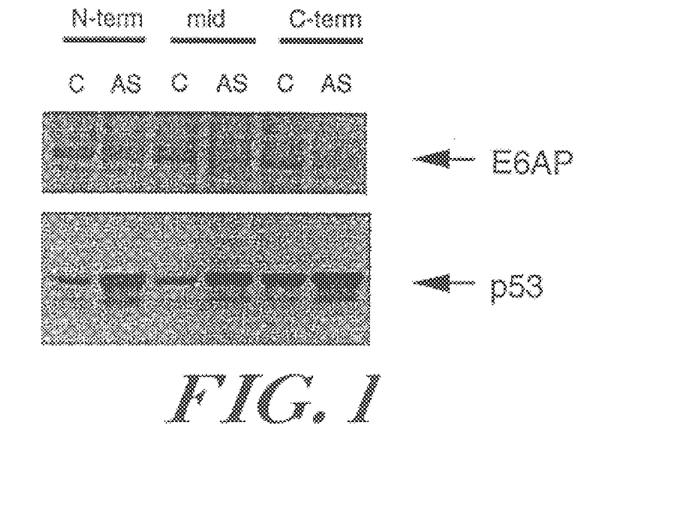
FIG. 1 depicts a Western blot of HeLa cell lysates from six separate transfections (C, control oligonucleotides (25–26 mers); AS, antisense oligonucleotides (25–26 mers) that targeted three different regions of an E6AP gene (N-terminal, middle, and C-terminal region of SEQ ID No: 1). Transfection with each of the three different AS oligonucleotides resulted in a down regulation of E6AP and marked increase in cellular p53 levels, as measured by immunoblotting.

Western blot of HeLa cell lysate was performed using standard protocols. Results of these experiments are presented in FIG. 1. Each antisense oligonucleotide used in the transfection experiments (AS4, AS6, AS8) caused down regulation of E6AP and led to a higher levels of p53 expression as compared to control oligonucleotides. The levels of E6AP and p53 were measured by immunoblotting.

All of the above-cited references and publications are hereby incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A purified preparation of an antisense nucleic acid which specifically hybridizes under physiological conditions to mRNA transcribed by gene encoding an E6-associated protein (an E6AP gene) and inhibits expression of said E6AP gene and wherein said antisense nucleic acid is further selected from the group consisting of a synthetic oligonucleotide, a single-stranded oligonucleotide, a linear oligonucleotide, an oligonucleotide which is 20–50 nucleotides in length, a DNA analog resistant to nuclease degradation, and combinations thereof.

2. The preparation of claim 1, which antisense nucleic acid is at least 20 nucleotides long.

3. The preparation of claim 1, which antisense nucleic acid is a DNA analog resistant to nuclease degradation.

4. The preparation of claim 1, which antisense nucleic acid specifically hybridizes to SEQ ID No:1.

5. The preparation of claim 4, which antisense nucleic acid comprises a nucleotide sequence complementary to at least 20 contiguous nucleotides from nucleotides 1–139 of SEQ ID No:1.

6. The preparation of claim 4, which antisense nucleic acid comprises a nucleotide sequence complementary to at least 20contiguous nucleotides from nucleotides 1100–1325 of SEQ ID No:1.

7. The preparation of claim 4, which antisense nucleic acid comprises a nucleotide sequence complementary to at least 20 contiguous nucleotides from nucleotides 2100–2316 of SEQ ID No:1.

8. An expression construct comprising a gene transcribable as an antisense nucleic acid which specifically hybridizes to mRNA expressed by a gene encoding an E6-associated protein (an E6AP gene) and inhibits expression of said E6AP gene under physiological conditions.

9. The expression construct of claim 8, wherein said nucleic acid specifically hybridizes to the nucleic acid sequence of SEQ ID No:1.

10. The expression construct of claim 9, wherein said antisense nucleic acid comprises a nucleotide sequence complementary to at least 20 contiguous nucleotides from nucleotides 1–139 of SEQ ID No:1.

11. The expression construct of claim 9, wherein said antisense nucleic acid comprises a nucleotide sequence complementary to at least 20 contiguous nucleotides from nucleotides 1100–1325 of SEQ ID No:1.

12. The expression construct of claim 9, wherein said antisense nucleic acid comprises a nucleotide sequence complementary to at least 20 contiguous nucleotides from nucleotides 2100–2316 of SEQ ID No:1.

13. A pharmaceutical composition comprising an antisense nucleic acid which specifically hybridizes to mRNA expressed by a gene encoding an E6-associated protein (an E6AP gene) and inhibits expression of E6AP gene under physiological conditions, which antisense nucleic acid is formulated in a pharmaceutically acceptable carrier.

14. A pharmaceutical composition comprising an expression construct including a gene transcribable as an antisense nucleic acid which specifically hybridizes to mRNA expressed by a gene encoding an E6-associated protein (an E6AP gene) and inhibits expression of said E6AP gene under physiological conditions, which expression construct is formulated in a pharmaceutically acceptable carrier.

15. An E6AP antisense nucleic acid having the nucleotide sequence of SEQ ID No:2.

16. An E6AP antisense nucleic acid having the nucleotide sequence of SEQ ID No:4.

17. An E6AP antisense nucleic acid having the nucleotide sequence of SEQ ID No:6.

18. A method of increasing a cellular p53 level of an epithelial cell comprising: introducing into an epithelial cell by topical application to said cell an E6AP antisense construct in an amount sufficient to produce in the cell a population of antisense nucleic acids which specifically hybridize to mFNA expressed by a gene encoding an E6-associated protein (an E6AP gene) under physiological conditions and which inhibit expression of said E6AP gene, wherein inhibition of expression of said E6AP gene results in a statistically significant increase in the cellular p53 level compared to a control population of cells.

19. The method of claim 18, wherein said antisense nucleic acid is cytotoxic to said cell.

20. The method of claim 18, wherein said antisense nucleic acid is cytostatic to said cell.

21. The method of claim 18, wherein said cell is a hyperproliferative epithelial cell.

22. The method of claim 18, wherein said cell is a p53+ transformed epithelial cell.

23. The method of claim 18, wherein said E6AP antisense construct is a synthetic antisense nucleic acid which specifically hybridizes to said E6AP gene.

24. The method of claim 23, wherein said antisense nucleic acid is at least 20 nucleotides long.

25. The method of claim 23, wherein said antisense nucleic acid is a DNA analog resistant to nuclease degradation.

26. The method of claim 18, wherein said E6AP construct is a gene construct comprising a gene transcribable as an antisense nucleic acid which specifically hybridizes to said E6AP gene.

27. A method of treating papillomavirus (PV) induced conditions comprising: administering to an animal, by topical application to cells infected with said papillomavirus, an E6AP antisense construct which inhibits expression of an E6AP gene in an amount sufficient to have a cytostatic or cgtotoxic effect on the PV-infected cells.

28. The method of claim 27, wherein said papilloma virus is a human papillomavirus (HPV).

29. The method of claim 28, wherein said HPV is a high risk HPV.

30. The method of claim 29, wherein said high risk HPV is selected from the group consisting of HPV-16, -18, -31 or -33.

31. The method of claim 28, wherein said HPV is a low risk HPV.

32. The method of claim 27, wherein said E6AP antisense construct is a synthetic antisense nucleic acid which specifically hybridizes to mRNA expressed by said E6AP gene.

33. The method of claim 32, wherein said antisense nucleic acid is at least 20 nucleotides long.

34. The method of claim 32, wherein said antisense nucleic acid is a DNA analog resistant to nuclease degradation.

35. The method of claim 27, wherein said E6AP construct is an expression construct comprising a gene transcribable as an antisense nucleic acid which specifically hybridizes to mRNA expressed by said E6AP gene.

36. A method of inhibiting proliferation of a cells expressing p53 comprising administering to an animal, by topical application to said cells, an E6AP antisense construct in an amount sufficient to produce in said cells a population of antisense nucleic acids which specifically hybridize to mRNA transcribed by a gene encoding an E6-associated protein (an _E6AP gene) under physiological conditions, which antisense nucleic acids inhibit expression of said E6AP gene inhibit proliferation of said cells.

37. The method of claim 36, wherein said cell is an epithelial cell.

38. The method of claim 36, wherein said E6AP antisense construct is a synthetic antisense nucleic acid which specifically hybridizes to MRNA expressed by said E6AP gene.

39. The method of claim 38, wherein said antisense nucleic acid is at least 20 nucleotides long.

40. The method of claim 36, wherein said antisense nucleic acid is a DNA analog resistant to nuclease degradation.

41. The method of claim 36, wherein said E6AP antisense construct is an expression construct comprising a gene transcribable as an antisense nucleic acid which specifically hybridizes to mRNA expressed by said E6AP gene.

42. The method of claim 36, wherein said E6AP antisense construct produces a cytostatic effect on said cell.

43. The method of claim 36, wherein said E6AP antisense construct produces a cytotoxic effect on said cell.

44. The preparation of any of claims 1, 4, 5, 6 or 7, which antisense nucleic acid is in the range of 20–50 nucleotides in length.

45. The preparation of claim 1, which antisense nucleic acid is a synthetic antisense nucleic acid.

46. The expression construct of claim 8, which expression construct comprises a viral vector.

47. The expression construct of claim 46, wherein the viral vector is selected from the group consisting of retroviral vectors, adenoviral vectors, adeno-associated viral vectors, herpes simplex viral vectors and vaccinia viral vectors.

48. The pharmaceutical composition of claim 13, wherein said antisense nucleic acid is in the range of 20–50 nucleotides in length.

49. The pharmaceutical composition of claim 13, wherein said antisense nucleic acid is a DNA analog resistant to nuclease degradation.

50. The pharmaceutical composition of claim 13, wherein said antisense nucleic acid is formulated as a cosmetic preparation.

51. The pharmaceutical composition of claim 13, wherein said antisense nucleic acid is formulated in an amount sufficient to produce a cytotoxic or cytostatic effect in cells infected with a wart virus.

52. The pharmaceutical composition of claim 51, wherein said wart virus is a papillomavirus.

53. The pharmaceutical composition of claim 51, wherein said cells are transformed by a papillomavirus.

54. The pharmaceutical composition of any of claims 13, 49, 50 or 51, wherein said antisense nucleic acid is formulated for topical administration.

55. The pharmaceutical composition of claim 54, wherein said antisense nucleic acid is formulated into an ointment, salve, gel or cream.

56. The pharmaceutical composition of claim 54, wherein said antisense nucleic acid is formulated into a liposome preparation.

57. The pharmaceutical composition of claim 14, wherein said expression construct comprises a viral vector.

58. The pharmaceutical composition of claim 57, wherein said viral vector is selected from the group consisting of retroviral vectors, adenoviral vectors, adeno-associated viral vectors, herpes simplex viral vectors and vaccinia viral vectors.

59. The pharmaceutical composition of claim 14, wherein said expression construct is formulated as a cosmetic preparation.

60. The pharmaceutical composition of claim 14, wherein said expression construct is formulated in an amount sufficient to produce a cytotoxic or cytostatic effect in cells infected with a wart virus.

61. The pharmaceutical composition of claim 60, wherein said wart virus is a papillomavirus.

62. The pharmaceutical composition of claim 60, wherein said cells are transformed by a papillomavirus.

63. The pharmaceutical composition of any of claims 14, 57, 59 or 60, wherein said expression construct is formulated for topical administration.

64. The pharmaceutical composition of claim 63, wherein said expression construct is formulated into an ointment, salve, gel or cream.

65. The pharmaceutical composition of claim 63, wherein said expression construct is formulated into a liposome preparation.

66. The method of claim 24, wherein said oligonucleotide is in the range of 20–50 nucleotides in length.

67. The method of claim 33, wherein said oligonucleotide is in the range of 20–50 nucleotides in length.

68. The method of claim 35, wherein said expression construct comprises a viral vector.

69. The method of claim 68, wherein said viral vector is selected from the group consisting of retroviral vectors, adenoviral vectors, adeno-associated viral vectors, herpes simplex viral vectors and vaccinia viral vectors.

70. The method of claim 27, wherein said PV-induced condition is a wart.

71. The method of claim 27, wherein said PV-induced condition is selected from the group consisting of laryngeal papilloma and cervical carcinoma.

72. The method of claim 32, wherein said oligonucleotide hybridizes to at least 20 contiguous nucleotides of an E6AP gene selected from the group consisting of nucleotides 1–139 of SEQ ID No:1, nucleotides 1100–1325 of SEQ ID No:1 and nucleotides 2100–2316 of SEQ ID No:1.

73. The method of claim 32, wherein said oligonucleotide has a nucleotide sequence represented by SEQ ID No:2, 4 or 6.

74. The method of claim 37, wherein the epithelial cells are of squamous epithelia.

75. The method of claim 37, wherein the epithelial cells are cutaneous epithelia.

76. The method of claim 73, wherein the epithelial cells are mucosal epithelia.

77. The method of any of claims 36, 37, 74, 75 or 76, wherein the cells are infected or transformed by a virus.

78. The method of claim 74, wherein the virus is a wart virus.

79. The method of claim 78, wherein the wart virus is a papillomavirus.

80. The method of claim 41, wherein said expression construct comprises a viral vector.

81. The method of claim 80, wherein said viral vector is selected from the group consisting of retroviral vectors, adenoviral vectors, adeno-associated viral vectors, herpes simplex viral vectors and vaccinia viral vectors.

82. The method of claim 39, wherein said oligonucleotide is in the range of 20–50 nucleotides in length.

83. The method of any of claims 36, 37 or 38, wherein said E6AP antisense construct is topically administered to said cells.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2625 base pairs
        ( B ) TYPE: nucleic acid
        ( C ) STRANDEDNESS: both
        ( D ) TOPOLOGY: linear     ( i i ) MOLECULE TYPE: cDNA     ( i x ) FEATURE:
        ( A ) NAME/KEY: CDS
        ( B ) LOCATION: 1..2622

( x i ) SEQUENCE DESCRIPTION: SEQ ID NO:1:

```
TCA GGA GAA CCT CAG TCT GAC GAC ATT GAA GCT AGC CGA ATG AAG CGA    48
Ser Gly Glu Pro Gln Ser Asp Asp Ile Glu Ala Ser Arg Met Lys Arg
 1               5                  10                  15

GCA GCT GCA AAG CAT CTA ATA GAA CGC TAC TAC CAC CAG TTA ACT GAG    96
Ala Ala Ala Lys His Leu Ile Glu Arg Tyr Tyr His Gln Leu Thr Glu
                20                  25                  30

GGC TGT GGA AAT GAA GCC TGC ACG AAT GAG TTT TGT GCT TCC TGT CCA   144
Gly Cys Gly Asn Glu Ala Cys Thr Asn Glu Phe Cys Ala Ser Cys Pro
             35                  40                  45

ACT TTT CTT CGT ATG GAT AAT AAT GCA GCA GCT ATT AAA GCC CTC GAG   192
Thr Phe Leu Arg Met Asp Asn Asn Ala Ala Ala Ile Lys Ala Leu Glu
     50                  55                  60

CTT TAT AAG ATT AAT GCA AAA CTC TGT GAT CCT CAT CCC TCC AAG AAA   240
Leu Tyr Lys Ile Asn Ala Lys Leu Cys Asp Pro His Pro Ser Lys Lys
 65                  70                  75                  80

GGA GCA AGC TCA GCT TAC CTT GAG AAC TCG AAA GGT GCC CCC AAC AAC   288
Gly Ala Ser Ser Ala Tyr Leu Glu Asn Ser Lys Gly Ala Pro Asn Asn
                 85                  90                  95

TCC TGC TCT GAG ATA AAA ATG AAC AAG AAA GGC GCT AGA ATT GAT TTT   336
Ser Cys Ser Glu Ile Lys Met Asn Lys Lys Gly Ala Arg Ile Asp Phe
            100                 105                 110

AAA GAT GTG ACT TAC TTA ACA GAA GAG AAG GTA TAT GAA ATT CTT GAA   384
Lys Asp Val Thr Tyr Leu Thr Glu Glu Lys Val Tyr Glu Ile Leu Glu
        115                 120                 125

TTA TGT AGA GAA AGA GAG GAT TAT TCC CCT TTA ATC CGT GTT ATT GGA   432
Leu Cys Arg Glu Arg Glu Asp Tyr Ser Pro Leu Ile Arg Val Ile Gly
    130                 135                 140

AGA GTT TTT TCT AGT GCT GAG GCA TTG GTA CAG AGC TTC CGG AAA GTT   480
Arg Val Phe Ser Ser Ala Glu Ala Leu Val Gln Ser Phe Arg Lys Val
145                 150                 155                 160

AAA CAA CAC ACC AAG GAA GAA CTG AAA TCT CTT CAA GCA AAA GAT GAA   528
Lys Gln His Thr Lys Glu Glu Leu Lys Ser Leu Gln Ala Lys Asp Glu
                165                 170                 175

GAC AAA GAT GAA GAT GAA AAG GAA AAA GCT GCA TGT TCT GCT GCT GCT   576
Asp Lys Asp Glu Asp Glu Lys Glu Lys Ala Ala Cys Ser Ala Ala Ala
            180                 185                 190

ATG GAA GAA GAC TCA GAA GCA TCT TCC TCA AGG ATA GGT GAT AGC TCA   624
Met Glu Glu Asp Ser Glu Ala Ser Ser Ser Arg Ile Gly Asp Ser Ser
        195                 200                 205

CAG GGA GAC AAC AAT TTG CAA AAA TTA GGC CCT GAT GAT GTG TCT GTG   672
Gln Gly Asp Asn Asn Leu Gln Lys Leu Gly Pro Asp Asp Val Ser Val
    210                 215                 220
```

| | | | | | | | | | | | | | | | | |
|---|---|---|---|---|---|---|---|---|---|---|---|---|---|---|---|---|
| GAT | ATT | GAT | GCC | ATT | AGA | AGG | GTC | TAC | ACC | AGA | TTG | CTC | TCT | AAT | GAA | 720 |
| Asp 225 | Ile | Asp | Ala | Ile 230 | Arg | Arg | Val | Tyr | Thr 235 | Arg | Leu | Leu | Ser | Asn | Glu 240 | |
| AAA | ATT | GAA | ACT | GCC | TTT | CTC | AAT | GCA | CTT | GTA | TAT | TTG | TCA | CCT | AAC | 768 |
| Lys | Ile | Glu | Thr | Ala 245 | Phe | Leu | Asn | Ala | Leu 250 | Val | Tyr | Leu | Ser | Pro 255 | Asn | |
| GTG | GAA | TGT | GAC | TTG | ACG | TAT | CAC | AAT | GTA | TAC | TCT | CGA | GAT | CCT | AAT | 816 |
| Val | Glu | Cys | Asp 260 | Leu | Thr | Tyr | His | Asn 265 | Val | Tyr | Ser | Arg | Asp 270 | Pro | Asn | |
| TAT | CTG | AAT | TTG | TTC | ATT | ATC | GGA | ATG | GAG | AAT | AGA | AAT | CTC | CAC | AGT | 864 |
| Tyr | Leu | Asn 275 | Leu | Phe | Ile | Ile | Gly 280 | Met | Glu | Asn | Arg | Asn 285 | Leu | His | Ser | |
| CCT | GAA | TAT | CTG | GAA | ATG | GCT | TTG | CCA | TTA | TTT | TGC | AAA | GCG | ATG | AGC | 912 |
| Pro | Glu 290 | Tyr | Leu | Glu | Met | Ala 295 | Leu | Pro | Leu | Phe | Cys 300 | Lys | Ala | Met | Ser | |
| AAG | CTA | CCC | CTT | GCA | GCC | CAA | GGA | AAA | CTG | ATC | AGA | CTG | TGG | TCT | AAA | 960 |
| Lys 305 | Leu | Pro | Leu | Ala | Ala 310 | Gln | Gly | Lys | Leu | Ile 315 | Arg | Leu | Trp | Ser | Lys 320 | |
| TAC | AAT | GCA | GAC | CAG | ATT | CGG | AGA | ATG | ATG | GAG | ACA | TTT | CAG | CAA | CTT | 1008 |
| Tyr | Asn | Ala | Asp | Gln 325 | Ile | Arg | Arg | Met | Met 330 | Glu | Thr | Phe | Gln | Gln 335 | Leu | |
| ATT | ACT | TAT | AAA | GTC | ATA | AGC | AAT | GAA | TTT | AAC | AGT | CGA | AAT | CTA | GTG | 1056 |
| Ile | Thr | Tyr | Lys 340 | Val | Ile | Ser | Asn | Glu 345 | Phe | Asn | Ser | Arg | Asn 350 | Leu | Val | |
| AAT | GAA | TTT | AAC | AGT | CGA | AAT | CTA | GTG | AAT | GAT | GAT | GAT | GCC | ATT | GTT | 1104 |
| Asn | Glu | Phe 355 | Asn | Ser | Arg | Asn | Leu 360 | Val | Asn | Asp | Asp | Asp 365 | Ala | Ile | Val | |
| GCT | GCT | TCG | AAG | TGC | TTG | AAA | ATG | GTT | TAC | TAT | GCA | AAT | GTA | GTG | GGA | 1152 |
| Ala | Ala | Ser 370 | Lys | Cys | Leu | Lys | Met 375 | Val | Tyr | Tyr | Ala | Asn 380 | Val | Val | Gly | |
| GGG | GAA | GTG | GAC | ACA | AAT | CAC | AAT | GAA | GAA | GAT | GAT | GAA | GAG | CCC | ATC | 1200 |
| Gly 385 | Glu | Val | Asp | Thr | Asn 390 | His | Asn | Glu | Glu | Asp 395 | Asp | Glu | Glu | Pro | Ile 400 | |
| CCT | GAG | TCC | AGC | GAG | CTG | ACA | CTT | CAG | GAA | CTT | TTG | GGA | GAA | GAA | AGA | 1248 |
| Pro | Glu | Ser | Ser | Glu 405 | Leu | Thr | Leu | Gln | Glu 410 | Leu | Leu | Gly | Glu | Glu 415 | Arg | |
| AGA | AAC | AAG | AAA | GGT | CTT | CGA | GTG | GAC | CCC | CTG | GAA | ACT | GAA | CTT | GGT | 1296 |
| Arg | Asn | Lys | Lys 420 | Gly | Leu | Arg | Val | Asp 425 | Pro | Leu | Glu | Thr | Glu 430 | Leu | Gly | |
| GTT | AAA | ACC | CTG | GAT | TGT | CGA | AAA | CCA | CTT | ATC | CCT | TTT | GAA | GAG | TTT | 1344 |
| Val | Lys | Thr 435 | Leu | Asp | Cys | Arg | Lys 440 | Pro | Leu | Ile | Pro | Phe 445 | Glu | Glu | Phe | |
| ATT | AAT | GAA | CCA | CTG | AAT | GAG | GTT | CTA | GAA | ATG | GAT | AAA | GAT | TAT | ACT | 1392 |
| Ile | Asn 450 | Glu | Pro | Leu | Asn | Glu 455 | Val | Leu | Glu | Met | Asp 460 | Lys | Asp | Tyr | Thr | |
| TTT | TTC | AAA | GTA | GAA | ACA | GAG | AAC | AAA | TTC | TCT | TTT | ATG | ACA | TGT | CCC | 1440 |
| Phe 465 | Phe | Lys | Val | Glu | Thr 470 | Glu | Asn | Lys | Phe | Ser 475 | Phe | Met | Thr | Cys | Pro 480 | |
| TTT | ATA | TTG | AAT | GCT | GTC | ACA | AAG | AAT | TTG | GGA | TTA | TAT | TAT | GAC | AAT | 1488 |
| Phe | Ile | Leu | Asn | Ala 485 | Val | Thr | Lys | Asn | Leu 490 | Gly | Leu | Tyr | Tyr | Asp 495 | Asn | |
| AGA | ATT | CGC | ATG | TAC | AGT | GAA | CGA | AGA | ATC | ACT | GTT | CTC | TAC | AGC | TTA | 1536 |
| Arg | Ile | Arg | Met | Tyr 500 | Ser | Glu | Arg | Arg | Ile 505 | Thr | Val | Leu | Tyr | Ser 510 | Leu | |
| GTT | CAA | GGA | CAG | CAG | TTG | AAT | CCA | TAT | TTG | AGA | CTC | AAA | GTT | AGA | CGT | 1584 |
| Val | Gln | Gly | Gln 515 | Gln | Leu | Asn | Pro | Tyr 520 | Leu | Arg | Leu | Lys | Val 525 | Arg | Arg | |
| GAC | CAT | ATC | ATA | GAT | GAT | GCA | CTT | GTC | CGG | CTA | GAG | ATG | ATC | GCT | ATG | 1632 |
| Asp | His | Ile | Ile 530 | Asp | Asp | Ala | Leu | Val 535 | Arg | Leu | Glu | Met | Ile 540 | Ala | Met | |

```
GAA  AAT  CCT  GCA  GAC  TTG  AAG  AAG  CAG  TTG  TAT  GTG  GAA  TTT  GAA  GGA   1680
Glu  Asn  Pro  Ala  Asp  Leu  Lys  Lys  Gln  Leu  Tyr  Val  Glu  Phe  Glu  Gly
545            550                 555                 560

GAA  CAA  GGA  GTT  GAT  GAG  GGA  GGT  GTT  TCC  AAA  GAA  TTT  TTT  CAG  CTG   1728
Glu  Gln  Gly  Val  Asp  Glu  Gly  Gly  Val  Ser  Lys  Glu  Phe  Phe  Gln  Leu
               565                 570                 575

GTT  GTG  GAG  GAA  ATC  TTC  AAT  CCA  GAT  ATT  GGT  ATG  TTC  ACA  TAC  GAT   1776
Val  Val  Glu  Glu  Ile  Phe  Asn  Pro  Asp  Ile  Gly  Met  Phe  Thr  Tyr  Asp
               580                 585                 590

GAA  TCT  ACA  AAA  TTG  TTT  TGG  TTT  AAT  CCA  TCT  TCT  TTT  GAA  ACA  GAG   1824
Glu  Ser  Thr  Lys  Leu  Phe  Trp  Phe  Asn  Pro  Ser  Ser  Phe  Glu  Thr  Glu
          595                 600                 605

GGT  CAG  TTT  ACT  CTG  ATT  GGC  ATA  GTA  CTG  GGT  CTG  GCT  ATT  TAC  AAT   1872
Gly  Gln  Phe  Thr  Leu  Ile  Gly  Ile  Val  Leu  Gly  Leu  Ala  Ile  Tyr  Asn
610                 615                 620

AAC  TGT  ATA  CTG  GAT  GTA  CAT  TTT  CCC  ATG  GTT  GTC  TAC  AGG  AAG  CTA   1920
Asn  Cys  Ile  Leu  Asp  Val  His  Phe  Pro  Met  Val  Val  Tyr  Arg  Lys  Leu
625                 630                 635                 640

ATG  GGG  AAA  AAA  GGA  CTT  TTC  GTC  GAC  TTG  GGA  GAC  TCT  CAC  CCA  GTT   1968
Met  Gly  Lys  Lys  Gly  Leu  Phe  Val  Asp  Leu  Gly  Asp  Ser  His  Pro  Val
               645                 650                 655

CTA  TAT  CAG  AGT  TTA  AAA  GAT  TTA  TTG  GAG  TAT  GTT  GGG  AAT  GTG  GAA   2016
Leu  Tyr  Gln  Ser  Leu  Lys  Asp  Leu  Leu  Glu  Tyr  Val  Gly  Asn  Val  Glu
          660                 665                 670

GAT  GAC  ATG  ATG  ATC  ACT  TTC  CAG  ATA  TCA  CAG  ACA  AAT  CTT  TTT  GGT   2064
Asp  Asp  Met  Met  Ile  Thr  Phe  Gln  Ile  Ser  Gln  Thr  Asn  Leu  Phe  Gly
               675                 680                 685

AAC  CCA  ATG  ATG  TAT  GAT  CTA  AAG  GAA  AAT  GGT  GAT  AAA  ATT  CCA  ATT   2112
Asn  Pro  Met  Met  Tyr  Asp  Leu  Lys  Glu  Asn  Gly  Asp  Lys  Ile  Pro  Ile
     690                 695                 700

ACA  AAT  GAA  AAC  AGG  AAG  GAA  TTT  GTC  AAT  CTT  TAT  TCT  GAC  TAC  ATT   2160
Thr  Asn  Glu  Asn  Arg  Lys  Glu  Phe  Val  Asn  Leu  Tyr  Ser  Asp  Tyr  Ile
705                 710                 715                 720

CTC  AAT  AAA  TCA  GTA  GAA  AAA  CAG  TTC  AAG  GCT  TTT  CGG  AGA  GGT  TTT   2208
Leu  Asn  Lys  Ser  Val  Glu  Lys  Gln  Phe  Lys  Ala  Phe  Arg  Arg  Gly  Phe
               725                 730                 735

CAT  ATG  GTG  ACC  AAT  GAA  TCT  CCC  TTA  AAG  TAC  TTA  TTC  AGA  CCA  GAA   2256
His  Met  Val  Thr  Asn  Glu  Ser  Pro  Leu  Lys  Tyr  Leu  Phe  Arg  Pro  Glu
               740                 745                 750

GAA  ATT  GAA  TTG  CTT  ATA  TGT  GGA  AGC  CGC  AAT  CTA  GAT  TTC  CAA  GCA   2304
Glu  Ile  Glu  Leu  Leu  Ile  Cys  Gly  Ser  Arg  Asn  Leu  Asp  Phe  Gln  Ala
          755                 760                 765

CTA  GAA  GAA  ACT  ACA  GAA  TAT  GAC  GGT  GGC  TAT  ACC  AGG  GAC  TCT  GTT   2352
Leu  Glu  Glu  Thr  Thr  Glu  Tyr  Asp  Gly  Gly  Tyr  Thr  Arg  Asp  Ser  Val
     770                 775                 780

CTG  ATT  AGG  GAG  TTC  TGG  GAA  ATC  GTT  CAT  TCA  TTT  ACA  GAT  GAA  CAG   2400
Leu  Ile  Arg  Glu  Phe  Trp  Glu  Ile  Val  His  Ser  Phe  Thr  Asp  Glu  Gln
785                 790                 795                 800

AAA  AGA  CTC  TTC  TTG  CAG  TTT  ACA  ACG  GGC  ACA  GAC  AGA  GCA  CCT  GTG   2448
Lys  Arg  Leu  Phe  Leu  Gln  Phe  Thr  Thr  Gly  Thr  Asp  Arg  Ala  Pro  Val
               805                 810                 815

GGA  GGA  CTA  GGA  AAA  TTA  AAG  ATG  ATT  ATA  GCC  AAA  AAT  GGC  CCA  GAC   2496
Gly  Gly  Leu  Gly  Lys  Leu  Lys  Met  Ile  Ile  Ala  Lys  Asn  Gly  Pro  Asp
               820                 825                 830

ACA  GAA  AGG  TTA  CCT  ACA  TCT  CAT  ACT  TGC  TTT  AAT  GTG  CTT  TTA  CTT   2544
Thr  Glu  Arg  Leu  Pro  Thr  Ser  His  Thr  Cys  Phe  Asn  Val  Leu  Leu  Leu
          835                 840                 845

CCG  GAA  TAC  TCA  AGC  AAA  GAA  AAA  CTT  AAA  GAG  AGA  TTG  TTG  AAG  GCC   2592
Pro  Glu  Tyr  Ser  Ser  Lys  Glu  Lys  Leu  Lys  Glu  Arg  Leu  Leu  Lys  Ala
850                 855                 860
```

| ATC | ACG | TAT | GCC | AAA | GGA | TTT | GGC | ATG | CTG | TAA | 2625 |
| Ile | Thr | Tyr | Ala | Lys | Gly | Phe | Gly | Met | Leu | | |
| 865 | | | | 870 | | | | | | | |

(2) INFORMATION FOR SEQ ID NO:2:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:2:

CGGCTAGCTT CAATGTCGTC AGACTG                          26

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:3:

GTCAGACTGC TGTAACTTCG ATCGGC                          26

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:4:

GAAGTGTCAG CTCGCTGGAC TCAGG                           25

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:5:

GGACTCAGGT CGCTCGACTG TGAAG                           25

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:6:

CCATATGAAA ACCTCTCCGA AAAGCC                          26

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:7:

CCGAAAAGCC TCTCCAAAAG TATACC        2 6